United States Patent
Subashi et al.

(10) Patent No.: US 10,524,689 B2
(45) Date of Patent: Jan. 7, 2020

(54) SELF-GATED INTERLEAVED RADIAL MRI FOR ABDOMINOTHORACIC IMAGING

(71) Applicant: Duke University, Durham, NC (US)

(72) Inventors: Ergys Subashi, Durham, NC (US); Jing Cai, Cary, NC (US)

(73) Assignee: Duke University, Durham, NC (US)

(*) Notice: Subject to any disclaimer, the term of this patent is extended or adjusted under 35 U.S.C. 154(b) by 376 days.

(21) Appl. No.: 15/600,041

(22) Filed: May 19, 2017

(65) Prior Publication Data
US 2017/0332939 A1    Nov. 23, 2017

Related U.S. Application Data

(60) Provisional application No. 62/338,595, filed on May 19, 2016.

(51) Int. Cl.
  *A61B 5/055* (2006.01)
  *G06T 7/30* (2017.01)
  *G01R 33/00* (2006.01)
(52) U.S. Cl.
  CPC .......... *A61B 5/055* (2013.01); *G01R 33/0029* (2013.01); *G01R 33/0035* (2013.01); *G01R 33/0041* (2013.01)
(58) Field of Classification Search
  CPC .. A61B 5/055; A61B 5/7207; G01R 33/0029; G01R 33/0035; G01R 33/0041
  See application file for complete search history.

(56) References Cited

U.S. PATENT DOCUMENTS

| | | | | |
|---|---|---|---|---|
| 2007/0038073 A1* | 2/2007 | Mistretta | ............... | A61B 5/055 600/410 |
| 2011/0251477 A1* | 10/2011 | Schmitt | ............... | A61B 5/0263 600/410 |

* cited by examiner

*Primary Examiner* — Michael T Rozanski
(74) *Attorney, Agent, or Firm* — McDonnell Boehnen Hulbert & Berghoff LLP

(57) ABSTRACT

The present disclosure provides, in part, methods for high spatiotemporal resolution self-sorted 4D MRI. These methods can be used to improve resolution of abdominothoracic MRI during breathing by facilitating the sorting of information corresponding to individual MRI pulse sequences according to phase within the respiratory cycle. An image of the anatomy for a particular phase within the respiratory cycle is then determined using both information corresponding to the particular phase and high-frequency MR imaging information corresponding to other respiratory phases. This method provides an increase in image resolution by sharing information at high frequencies in k-space, which may be less thoroughly sampled during any particular respiratory phase, between different respiratory phases. Methods herein also permit use of DC information from individual MRI pulse sequences to determine respiratory tissue motion and to use this tissue motion information to sort the individual MRI pulse sequences according to respiratory cycle phase.

20 Claims, 6 Drawing Sheets

SELF-GATED INTERLEAVED RADIAL MRI FOR ABDOMINOTHORACIC IMAGING

CROSS-REFERENCE TO RELATED APPLICATION

This application claims the benefit of and incorporates by reference the content of U.S. Provisional Pat. App. No. 62/338,595, filed May 19, 2016.

BACKGROUND

Unless otherwise indicated herein, the materials described in this section are not prior art to the claims in this application and are not admitted to be prior art by inclusion in this section.

The accuracy and precision of many therapeutic imaging interventions is challenged by respiratory motion. Ventilation-induced tumor and organ-at-risk oscillations are of concern primarily for imaging lung and upper abdominal malignancies. Four dimensional (4D) computerized tomography (CT) is currently the most widely adopted modality for imaging organs that are subject to respiratory motion. However, the mechanical design of CT scanners limits the sampling pattern and often leads to resampling artifacts. This modality also provides poor soft tissue contrast.

Magnetic resonance imaging (MRI) can provide improved soft tissue contrast relative to CT. Further, the sampling function of an MR imager can be easily modified and adapted to, e.g., facilitate imaging of particular portions of anatomy, to detect a flow tensor or other specialized properties of tissue, to emphasize imaging of certain types of tissue or contrast agents, or to provide some other benefit. However, MRI can impose strict timing requirements when imaging tissue, requiring extensive time for acquisition and/or numerous MR scans to generate an adequate image of tissue. These factors have limited application of MRI to the imaging of tissues that are in motion, for example, the lungs, heart, and other tissues of the abdominal and/or thoracic cavities during respiration.

SUMMARY

The present disclosure provides a variety of methods using magnetic resonance imaging (MRI) to image abdominothoracic organs, tumors, or other biological tissues while compensating for respiratory-induced motion. The techniques disclosed herein facilitate imaging of such tissues more quickly than other contemporary techniques without compromising spatial resolution or imaging volume/coverage. Alternatively, for a given total scan time, the techniques disclosed herein facilitate a greater imaging volume/coverage and spatial resolution than other contemporary techniques. Images generated according to the techniques disclosed herein provide high levels of soft tissue contrast without the use of ionizing radiation. Further, the techniques disclosed herein may be adapted to a variety of pulse sequences to exploit various contrast mechanisms inherent in living tissue, allowing the techniques disclosed herein to be applied toward imaging a variety of different tissue properties.

One aspect of the present disclosure provides a method including: (i) obtaining interaction information indicative of a plurality of interactions between a biological tissue and respective different magnetic resonance imaging pulse sequences; (ii) obtaining a respiratory signal related to respiratory activity of the biological tissue; (iii) based on the respiratory signal, selecting a respective reference phase for each of the magnetic resonance imaging pulse sequences, where the respective reference phases are selected from a plurality of respiratory phases; and (iv) generating a first image of the biological tissue for a first reference phase in the plurality of respiratory phases. The obtained interaction information includes imaging information about the biological tissue at discrete points along a plurality of different radial trajectories in k-space, with each magnetic resonance imaging pulse sequence corresponding to a respective one of the radial trajectories in k-space. Generating the first image includes generating imaging information about the biological tissue during the first reference phase at a set of points in k-space based on a first portion of the obtained interaction information and a second portion of the obtained interaction information, wherein the first portion includes information about at least two magnetic resonance imaging pulse sequences corresponding to the first reference phase and the second portion includes information about at least one of the magnetic resonance imaging pulse sequences corresponding to a second reference phase that differs from the first reference phase. Generating the first image additionally includes transforming the generated imaging information to generate the first image.

Another aspect of the present disclosure provides a non-transitory computer-readable medium having instructions stored thereon that, upon execution by at least one processor, causes performance of operations. The operations include: (i) obtaining interaction information indicative of a plurality of interactions between a biological tissue and respective different magnetic resonance imaging pulse sequences; (ii) obtaining a respiratory signal related to respiratory activity of the biological tissue; (iii) based on the respiratory signal, selecting a respective reference phase for each of the magnetic resonance imaging pulse sequences, where the respective reference phases are selected from a plurality of respiratory phases; and (iv) generating a first image of the biological tissue for a first reference phase in the plurality of respiratory phases. The obtained interaction information includes imaging information about the biological tissue at discrete points along a plurality of different radial trajectories in k-space, with each magnetic resonance imaging pulse sequence corresponding to a respective one of the radial trajectories in k-space. Generating the first image includes generating imaging information about the biological tissue during the first reference phase at a set of points in k-space based on a first portion of the obtained interaction information and a second portion of the obtained interaction information, where the first portion includes information about at least two magnetic resonance imaging pulse sequences corresponding to the first reference phase, and the second portion includes information about at least one of the magnetic resonance imaging pulse sequences corresponding to a second reference phase that differs from the first reference phase. Generating the first image additionally includes transforming the generated imaging information to generate the first image.

Yet another aspect of the present disclosure provides a method including: (i) causing a pulse generator to emit a plurality of different magnetic resonance imaging pulse sequences such that the plurality of magnetic resonance imaging pulse sequences interact with a biological tissue, where each magnetic resonance imaging pulse sequence corresponds to a respective radial trajectory in k-space; (ii) obtaining interaction information indicative of a plurality of interactions between the biological tissue and the magnetic resonance imaging pulse sequences; (iii) obtaining a respiratory signal related to respiratory activity of the biological tissue; (iv) based on the respiratory signal, selecting a respective reference phase for each of the magnetic resonance imaging pulse sequences, where the respective reference phases are selected from a plurality of respiratory phases; and (v) generating a first image of the biological tissue for a first reference phase in the plurality of respiratory phases. The obtained interaction information includes imaging information about the biological tissue at discrete points along a plurality of different radial trajectories in k-space, with each of the different radial trajectories in k-space corresponding to at least one of the magnetic resonance imaging pulse sequences. Generating the first image includes generating imaging information about the biological tissue during the first reference phase at a set of points in k-space based on a first portion of the obtained interaction information and a second portion of the obtained interaction information, where the first portion includes information about at least two magnetic resonance imaging pulse sequences corresponding to the first reference phase and the second portion includes information about at least one of the magnetic resonance imaging pulse sequences corresponding to a second reference phase that differs from the first reference phase. Generating the first image additionally includes transforming the generated imaging information to generate the first image.

These as well as other aspects, advantages, and alternatives, will become apparent to those of ordinary skill in the art by reading the following detailed description, with reference where appropriate to the accompanying drawings.

DETAILED DESCRIPTION

Figure 1A:
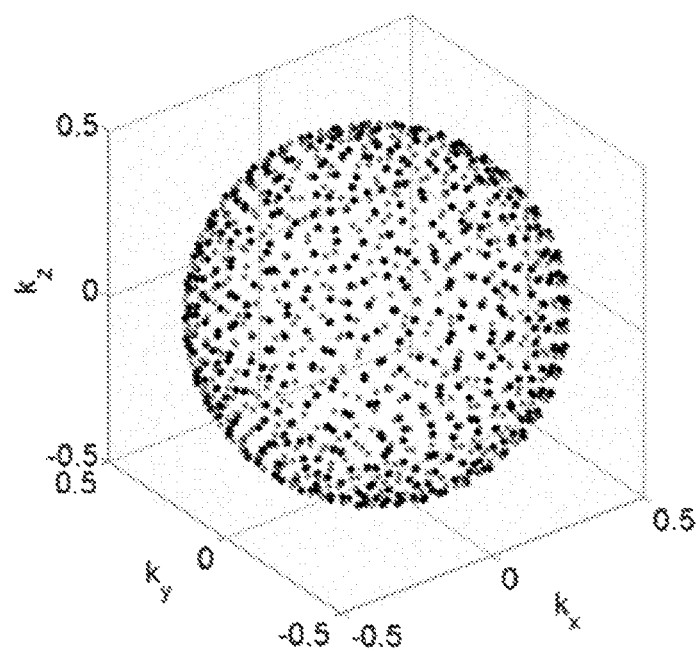
FIG. 1A shows a sampling of angles in k-space.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

The present disclosure provides a self-sorting, high-resolution 4D-MRI imaging method that has an acquisition time comparable to that of 4D CT. The methods disclosed include sorting information from a plurality of magnetic-resonance imaging (MRI) pulse sequences according to phase within the respiratory cycle and then generating, based on that sortition, images of the lungs and other abdominothoracic anatomy for one or more phases within the respiratory cycle. For example, one of the phases within the respiratory cycle could correspond to a person maximally exhaling (e.g., to the lungs having a minimal volume) and the method could include generating an image of the lungs when the lungs have minimal volume (i.e., when the person is exhaling).

The method uses detected radio-frequency signals emitted from a biological tissue (e.g., from lungs or other abdominothoracic tissues) or other information about interactions between the biological tissue and a plurality of different MRI pulse sequences to generate images of the biological tissue. Each such MRI pulse sequence corresponds to a respective radial trajectory in k-space and may be an Archimedian spiral trajectory, a golden spiral trajectory, some other spiral trajectory, a linear trajectory, a center-out trajectory, a periphery-center-periphery trajectory, or some other radial trajectory that includes a portion near the origin of k-space and a portion near a peripheral region of k-space that is separated from the origin of k-space. A given MRI pulse sequence corresponds to a particular respective trajectory in k-space. Thus, information about radio frequency signals responsively emitted from the biological tissue, or some other information indicative of an interaction between the given MRI pulse sequence and the biological tissue, provides information in k-space, along the particular trajectory in k-space, about the composition of the biological tissue during a period of time during which the given MRI pulse sequence is emitted. For example, the interaction information corresponding to a particular MRI pulse sequence could include information about the biological tissue (e.g., information about the proton density of the biological tissue) at a number of discrete points within k-space along the radial trajectory that corresponds to the particular MRI pulse sequence.

A respiratory signal related to a person's breathing (e.g., related to their status or phasing within the respiratory cycle) could be obtained and used to sort k-space data or other information related to interactions between the biological tissue of the person and the MRI pulse sequences according to their phasing within the respiratory cycle (e.g., to determine which of the MRI pulse sequences correspond in time to a first reference phase that, e.g., corresponds to the maximum exhalation). For example, a reference phase could be selected from a plurality of respiratory phases for each of the MRI pulse sequences.

Such a respiratory signal could be detected using a chest band, an EMG sensor, a camera, or some other sensor adapted to detect respiratory status/activity of a person. Additionally or alternatively, such a respiratory signal could be determined from the MRI interaction information directly. For example, information about the center of k-space (e.g., the DC component of k-space) as determined from interaction information corresponding to the interactions between the biological tissue and each of the MRI pulse sequences could be used to generate a respiratory signal that is related to the phase of the biological tissue within the respiratory cycle.

An image of the lungs or other biological tissue during a particular reference phase can then be determined, based on the interaction information indicative of those MRI pulse sequences that correspond to the particular reference sequence. This could include first generating imaging information about the biological tissue during the particular reference phase, e.g., by collating, filtering, upsampling, re-gridding, or performing some other process on the interaction information. The generated information could then be transformed, e.g., using a Fourier transformation, to generate an image of the biological tissue. In order to improve the image, interaction information from other reference phases (e.g., references phases other than the particular reference phase) could also be used to generate the imaging information about the biological tissue during the particular reference phase. Such a process may be referred to as "view sharing." Such a process could include using interaction information corresponding to higher frequencies in k-space from other reference phases. In some embodiments, interaction information corresponding to points in k-space that are separated from the origin by more than a threshold frequency could be used from reference phases other than the particular reference phase to generate the imaging information about the biological tissue during the particular reference phase. Such a threshold frequency could be uniform across MRI pulse sequences and/or reference phases alternative to the particular reference phase. Alternatively, different threshold frequencies could be applied to different MRI pulse sequences, e.g., on an individual bases, according to reference phase, or according to some other method.

Note that the methods described herein could be used to generate images of a variety of different tissues undergoing a variety of different stereotyped (e.g., cyclical) motions or changes. For example, the methods described herein could be used to generate images of a heart at a variety of points during a cardiac cycle, of a limb or a joint of a limb at a variety of points during a repeated or non-repeated motion, or to generate images of some other biological tissue at a variety of different phases within a repeated cyclical activity of the anatomy and/or at a variety of different states along a one-, two-, or more-dimensional manifold of characteristic states that may be occupied by the tissue. While reference will be made throughout this disclosure to imaging of abdominothoracic anatomy at reference phases within the respiratory cycle, it is to be understood that these methods may be applied without prejudice to such alternative portions of human or animal anatomy across such alternative repeating or non-repeating behaviors or anatomical changes.

Such methods and systems could, for example, include sorting information about the interaction between the biological tissue and a plurality of MRI pulse sequences (e.g., information about radio frequency pulses emitted from the biological tissue responsive to such pulse sequences) according to a signal related to the timing of a cycle of repeated activity, a signal related to the tissue status (e.g., to a joint angle), or related to some other information of interest about the biological tissue. The sorted information could then be used, according to the methods described herein, to generate one or more images of the biological tissue at one or more phases within a cycle of repeated activity or at one or more characteristic states or angles of interest. In such scenarios, example methods could include generating an image for a particular reference phase within a cycle of repeated activity (or at a particular reference angle within a range of angles, or at some other reference state within a range of possible states of the tissue) using a combination of (a) the interaction information corresponding to that particular reference phase (i.e., information at both higher and lower frequencies within k-space, including information at or near the origin of k-space); and (b) information at higher frequencies within k-space from interaction information that corresponds to reference phases other than the particular reference phase.

II. Binning and View Sharing of MRI Scan Data According to Respiratory Phase

The methods disclosed herein include obtaining information about interactions between a biological tissue and a plurality of different MRI pulse sequences to generate images of the biological tissue. Each such MRI pulse sequence can correspond to a respective different radial trajectory in k-space. Thus, information about radio frequency signals responsively emitted from the biological tissue, or some other information indicative of an interaction between the given MRI pulse sequence and the biological tissue, provides information in k-space, along the particular trajectory in k-space, about the composition of the biological tissue during a period of time during which the given MRI pulse sequence is emitted. Information about a plurality of such interactions, corresponding to a variety of different trajectories through k-space such that the k-space is adequately sampled, may permit generation of images having a specified noise level, resolution, field of view, or other properties.

Obtaining information about interactions between a biological tissue and a plurality of different MRI pulse sequences could include causing a pulse generator (e.g., a pulse generator coupled to one or more gradient coils, RF excitation coils, or other MR imaging apparatus) to emit the MRI pulse sequences, operating one or more RF receive coils to detect RF signals emitted from a biological tissue in response to exposure to such pulse sequences, or operating some other elements of an MR imaging system. Additionally or alternatively, obtaining information about interactions between a biological tissue and a plurality of different MRI pulse sequences could include receiving information (e.g., samples at discrete locations in k-space that represent proton densities) from an MR imager that is configured to provide such pulses and/or detect such RF signals, receiving information from a server that is in communication with an MR imager, receiving information from a data storage (e.g., archival information from past MR imaging sessions), or receiving information from some other system.

In examples wherein the biological tissue is in motion (e.g., where the biological tissue includes lungs or other abdominothoracic tissues undergoing respiration-related cyclic motion) or otherwise changing between a number of configurations (e.g., a number of different joint angles of a limb, a repeated cycle of peristalsis or chewing), each of the MRI pulse sequences could be sorted according to a reference phase related to the motion (e.g., a reference phase could be selected for each of the MRI pulse sequences). For example, a first reference phase corresponding to complete exhalation could be selected for each MRI pulse sequence that was applied to a person when the person was exhaling completely or nearly completely. Such sorting could be performed based on a variety of different information sources about the configuration of the biological tissue, e.g., a chest band or respirometer to detect a respiratory status, a goniometer to detect a joint angle. In some examples, information about the interaction between the MRI pulse sequences and the biological tissue could be used to sort the interaction information (e.g., a magnitude of the interaction between the biological tissue and the MRI pulse sequences near the origin of k-space could be used to determine phasing within a respiratory cycle).

Obtained information (e.g., detected RF pulses emitted from the person in response to exposure to such MRI pulse sequences) corresponding to such MRI pulse sequences could then be used to generate an image of the person's chest or other biological tissues when the person is exhaling completely. Additional images of the person's chest, when the person's chest is at different phases within a respiratory cycle (e.g., complete inhalation, partial exhalation, partial inhalation), could be generated based on interaction information that corresponds to those additional phases.

FIG. 1A shows a plurality of angles in k-space. Each of the indicated angles characterizes a radial trajectory, in k-space, of a respective MRI pulse sequence. Such characterization could include specifying polar and azimuthal angles of a center-out radial trajectory, polar and azimuthal angles of a terminal point of a center-out spiral trajectory (e.g., an Archimedian spiral, a golden-means trajectory), polar and azimuthal angles of a plane in k-space that encompasses a spiral trajectory, or could include characterizing a k-space trajectory, in terms of two or more angles in k-space, in some other manner.

Each MRI pulse sequence, corresponding to one of the illustrated angles/trajectories in k-space, is presented to a biological tissue during a respective period of time. The biological tissue may change configuration over time (e.g., may execute repeated respiratory cycles) such that each of the MRI pulse sequences corresponds to respective different configuration of the biological tissue (e.g., a respective different reference phase within a respiratory cycle). For example, the biological tissue could include lungs or other abdominothoracic tissues that move through a respiratory cycle. Such a respiratory cycle could be partitioned into a number of different reference phases (e.g., ten reference phases).

Figure 1B:
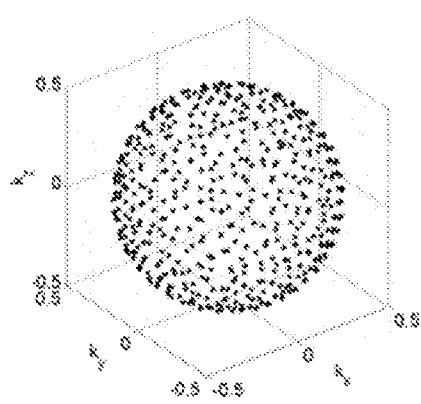
FIG. 1B shows a subset of the angles shown in FIG. 1A.
Figure 1C:
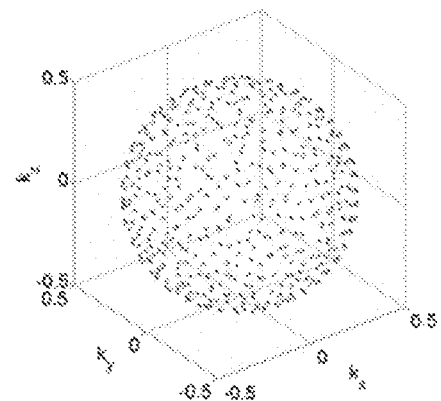
FIG. 1C shows a subset of the angles shown in FIG. 1A.
Figure 1D:
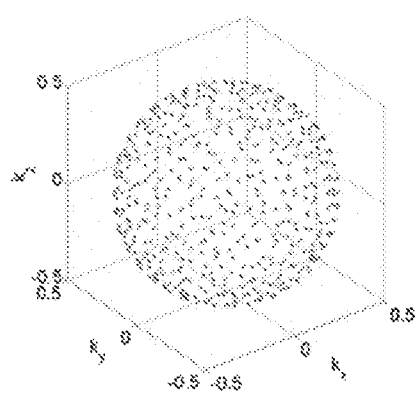
FIG. 1D shows a subset of the angles shown in FIG. 1A.
Figure 1E:
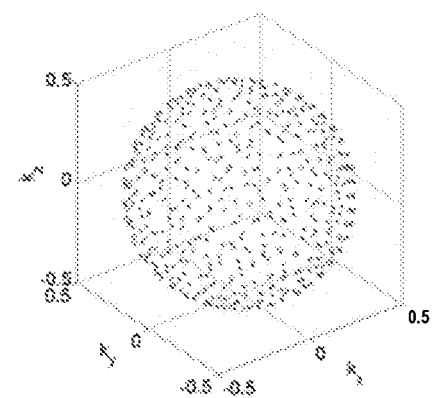
FIG. 1E shows a subset of the angles shown in FIG. 1A.

As an illustrative example, the respiratory phase could be partitioned into four different reference phases. Thus, a subset (indicated by the black dots in FIG. 1A) of the MRI pulse sequences could correspond to a first reference phase. FIG. 1B shows this subset of the angles in k-space. FIGS. 1C-1E show respective different, non-overlapping subsets of the pulse sequences shown in FIG. 1A that correspond to respective second, third, and fourth reference phases.

The angles of the trajectories, their ordering over time, or some other properties of the MRI pulse sequences could be specified to improve coverage of k-space, to reduce motion artifacts (e.g., artifacts related to correlations between the sampled angles and motion of the biological tissue), to improve resolution or noise characteristics of generated images of the biological tissue, or to provide some other benefits. Specifying such properties could include determining the angles of the trajectories and/or the sequence according to which the corresponding MRI pulse sequences are presented to the biological tissue according to a random distribution, a pseudo-random distribution, a quasi-random distribution, or some other non-periodic scheme. Such a scheme could be determined contemporaneously with presentation of the MRI pulse sequences to the biological tissue and/or could be pre-determined. Such a scheme could be selected to reduce a probability that the sampling of k-space by trajectories corresponding to any of the reference phases is significantly correlated to the reference phase (e.g., such that the pattern of k-space trajectories that sample each of the reference phases is substantially independent of the identity of the reference phase) and/or to improve an overall amount or uniformity of sampling of each of the reference phases within k-space.

To provide an image of the biological tissue for a first reference phase (or for some other reference phase of a set of reference phases, e.g., a set of respiratory phases), imaging information about the biological tissue during the first reference phase could be generated. Generation of such imaging information could include generating samples representing proton density or some other imaging information about the biological tissue at a set of points within k-space. For example, imaging information could be determined at a plurality of points in k-space corresponding to the discrete points in k-space that are described by the interaction information corresponding to the MRI pulse sequences that, themselves, correspond to the first reference phase. The generated imaging information could then be used to generate an image of the biological tissue.

Generating an image of the biological tissue, based on the generated imaging information, could include using a Fourier transform or some other method to generate an image. In some examples, generating an image of the biological tissue could include using a filter, interpolation, extrapolation, and/or other methods to generate further imaging information about the biological tissue at a second set of points in k-space. The second set of points in k-space could be arranged within k-space as a regular, orthogonal grid, e.g., the imaging information at the first set of points in k-space could be re-gridded to generate the further imaging information at the second set of points in k-space. An image of the biological tissue could then be generated, using a fast Fourier transform or some other technique, based on the further imaging information.

Figure 2A:
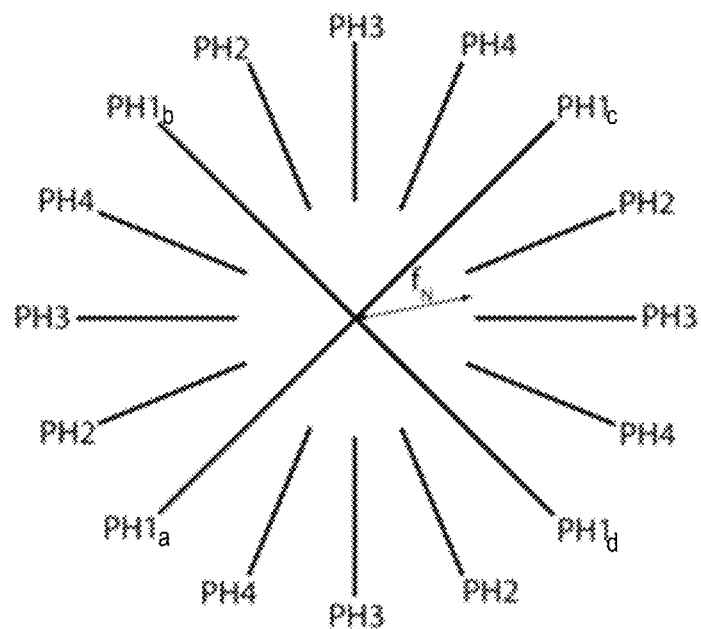
FIG. 2A shows trajectories in k-space.

FIG. 2A shows example radial trajectories, $PH1_a$-$PH1_d$, in a 2-dimensional k-space. The example radial trajectories $PH1_a$-$PH1_d$ span from the origin of the k-space to respective different points at the periphery of the k-space along respective different angles in k-space. The radial trajectories $PH1_a$-$PH1_d$ correspond to MRI pulse sequences applied to a biological tissue during a first reference phase. Information about interactions between the biological tissue and the MRI pulse sequences could represent information about the biological tissue at discrete points in k-space along the trajectories PH1$_a$-PH1$_d$. Such information could be used to generate imaging information about the biological tissue during the first reference phase as described elsewhere herein.

As shown in FIG. 2A, the radial trajectories that correspond to the first reference phase sample the periphery of k-space (i.e., regions farther from the origin of k-space) less (e.g., as a density of samples in k-space) than the region near the origin of k-space. In order to generate an improved image of the biological tissue during the first reference phase, information from the periphery of k-space during alternative reference phases could be used to generate imaging information about the biological tissue during the first reference phase.

Such additional information is indicated in FIG. 2A by the additional radial trajectories, PH2-PH3. The example radial trajectories PH2-PH4 span from a specified distance in k-space from the origin of k-space to respective different points at the periphery of the k-space along respective different angles in k-space. The radial trajectories PH2-PH4 correspond to MRI pulse sequences applied to the biological tissue during a respective second, third, and fourth reference phases. Information about interactions between the biological tissue and these additional MRI pulse sequences could represent information about the biological tissue at discrete points in k-space along the trajectories PH2-PH4 that are separated from the origin of k-space by more than a specified amount, e.g., by more than the indicated threshold frequency $f_N$. Such information could be used, in combination with the imaging information from PH1$_a$-PH1$_d$, to generate imaging information about the biological tissue during the first reference phase.

As shown in FIG. 2A, a single threshold frequency is applied to all of the alternative reference phases in order to determine what portion of the interaction information from the alternative reference phases (e.g., the portions corresponding to higher-frequency points in k-space) is used to determine imaging information for the first reference phase. Such a threshold frequency could be selected to ensure that the information used to generate an image of the biological tissue samples the k-space at or above the Nyquist frequency.

Alternatively, different threshold frequencies or other characteristics could be determined for each alternative reference phase and used to determine what portion of the interaction information from the alternative reference phases is used to determine imaging information for the first reference phase. For example, a threshold frequency could be determined for each of the alternative reference phases, PH2-PH4, according to:

$$f_i = f_N + \delta_i(k_{max} - f_N)$$

where $f_i$ is the threshold frequency applied to interaction information corresponding to MRI pulse sequences that, themselves, correspond to the $i^{th}$ reference phase; $f_N$ is a baseline frequency (e.g., determined to correspond to the Nyquist frequency for sampling the k-space), $\delta_i$ is a parameter that determines how far from the origin in k-space information from the $i^{th}$ reference phase must be to be included in the determination of imaging information for the first reference phase (or for some other given reference phase of interest), and $k_{max}$ is a maximum frequency of the trajectories in k-space. This frequency threshold-based filtering is generally not applied to the interaction information from a particular reference phase when the particular reference phase is being reconstructed.

In order for none of the information from alternative reference phases to be used in determination of imaging information for the first reference phase (e.g., to use no view-sharing in generating an image of the biological tissue during the first reference phase), $\delta_i$ may be set to 1 for all alternative reference phases. To use an equal amount of information from all of the alternative reference phases (e.g., to use uniform view-sharing), as illustrated in FIG. 2A, $\delta_i$ may be set to 0 for all alternative reference phases. In order to use different amounts of information from each of the alternative reference phases, $\delta_i$ may be set individually for each of the alternative reference phases.

Figure 2B:
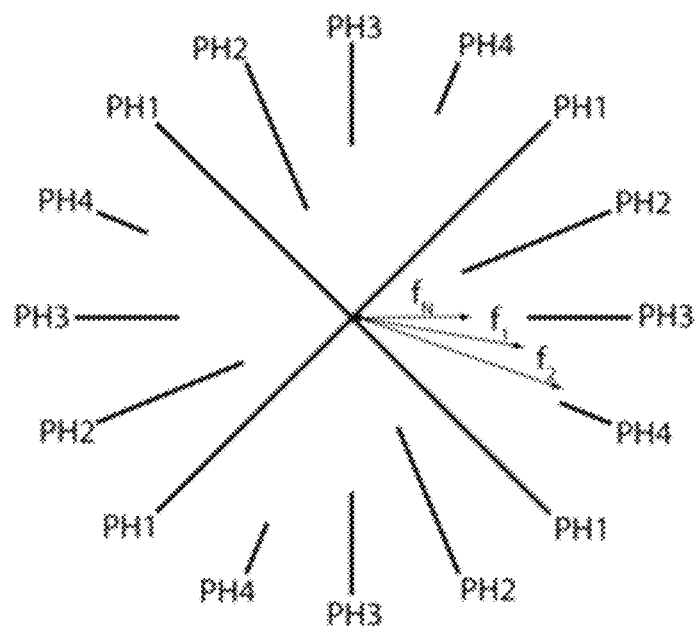
FIG. 2B shows trajectories in k-space.

The use of phase-dependent amounts of information from alternative reference phases is illustrated in FIG. 2B, which shows example radial trajectories, PH1$_a$-PH1$_d$, in a 2-dimensional k-space. The radial trajectories PH1$_a$-PH1$_d$ correspond to MRI pulse sequences applied to a biological tissue during a first reference phase. FIG. 2B also shows additional radial trajectories, PH2-PH3. The additional radial trajectories PH2-PH4 correspond to MRI pulse sequences applied to the biological tissue during a respective second, third, and fourth reference phases. Information about interactions between the biological tissue and the MRI pulse sequences could be used to generate imaging information for the biological tissue during the first reference phase. As shown, all of the interaction information from the first reference phase, PH1$_a$-PH1$_d$, is used to generate the imaging information, while portions of the interaction information above respective different threshold frequencies from each of the alternative reference phases is used to generate the imaging information. The most interaction information is retained from the second reference phase PH2 ($\delta_2$ has been set to 0), while less information, corresponding to points separated from the origin of k-space by greater threshold frequencies, is retained from the other reference phases PH3 and PH4 ($\delta_3$ and $\delta_4$ have been set to respective different values between 0 and 1).

These different $\delta_i$, threshold frequencies, or other characteristics determining the degree or portion of interaction information to share between reference phases could be determined in a variety of ways. In some examples, such a degree of view-sharing could be determined based on a degree of similarity between the configuration of the biological tissue during the different reference phases. Such a degree of similarity could be inferred from a difference in value of a signal related to motion or status of the biological tissue, e.g., related to a respiratory signal that is used to determine the respiratory phase of abdominothoracic tissues. Such a respiratory signal could be determined from one or more sensors used to detect respiratory activity and/or from the detected interaction information corresponding to the MRI pulse sequences during each of the reference phases.

Figure 3A:
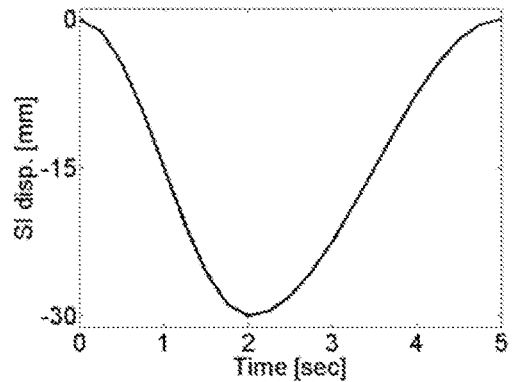
FIG. 3A shows a diaphragm motion curve.

FIG. 3A illustrates an example respiratory signal over time. The example respiratory signal could represent a variety of information about a biological tissue over time during a single respiratory cycle, e.g., a displacement in space of a particular portion of lung tissue over time, a DC-component in k-space of the interaction between the biological tissue an MRI pulse sequences over time, or some other measure related to the variation in the biological tissue over time as a function of respiration.

Figure 3B:
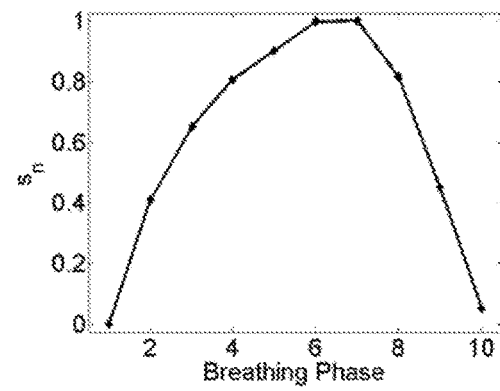
FIG. 3B shows an average breathing signal as a function of respiratory phase.
Figure 3C:
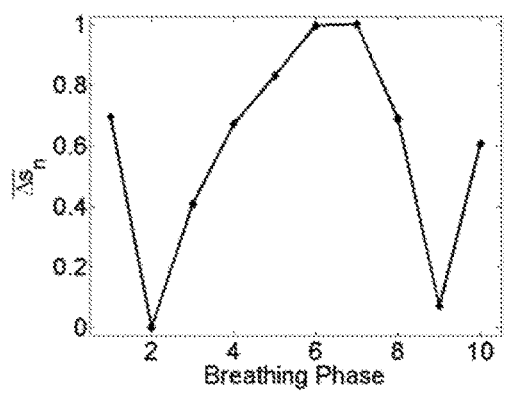
FIG. 3C shows a differential average breathing signal as a function of respiratory phase.

Such a respiratory signal could be used to determine a normalized difference between the biological tissue across different reference phases. For example, a mean normalized difference between the respiratory signal during each of the different reference phases could be determined. This is illustrated in FIG. 3B, which shows a normalized difference, $s_n$, between the average respiratory signal during each of ten different reference phases and the average respiratory signal during a first reference phase (thus, $s_1$ is zero). The normalized difference could be used to determine a degree or amount of interaction information from alternative reference phases to use in generating an image of a biological tissue during a particular reference phase. For example, FIG. 3C shows a differential normalized difference, $\overline{\Delta s_n}$, determined for a second reference phase based on the normalized difference between $s_2$ from FIG. 3B and each of the other $s_n$ in FIG. 3B (thus, $s_2$ is zero). Such a differential normalized difference could then be used to determine $\delta_2$ or to determine some other characteristic related to the degree or portion of interaction information corresponding to an alternative reference phase that is used to generate imaging information for a given reference phase.

As shown in FIG. 2B, a threshold frequency or other characteristic determining a degree of view sharing between MRI pulse sequences corresponding to different reference phases may be set on a per-phase basis. That is, to determine imaging information for a first reference phase, an amount of interaction information from MRI pulse sequences of an alternative reference phase (and thus a corresponding amount of "view-sharing" between the first and second reference phases) may be the same across all of the MRI pulse sequences of the alternative reference phase. Additionally or alternatively, the amount of interaction information used may be determined individually for each of the MRI pulse sequences.

For example, a threshold frequency could be determined for a particular MRI pulse sequence based on a portion of a respiratory signal corresponding to a period of time during which the biological tissue was exposed to the particular MRI pulse sequence. The threshold frequency could then be used to determine which portion of the interaction information that corresponds to the particular MRI pulse sequence to use in generating an image of the biological tissue during a particular reference phase. Determining such a threshold frequency could include determining a difference between the respiratory signal corresponding to the particular MRI pulse sequence and an average value of portions of the respiratory signal corresponding to the particular reference phase. Such a determined difference could be related to a difference in similarity between the configuration of the biological tissue during when the biological tissue was exposed to the particular MRI pulse sequence and the average configuration of the biological tissue during the particular reference phase.

III. Determining Respiratory Phase from MRI Scan Data

A respiratory signal used to select reference phases for MRI pulse sequences, to determine threshold frequencies for view sharing between such reference phases, or to facilitate some other applications could be obtained according to a variety of methods. Such methods could include operating a chest band, a spirometer, a camera, or some other sensor to detect one or more signals related to a respiratory activity, status, or configuration of a person's lungs and/or abdominothoracic tissue. Additionally or alternatively, such a respiratory signal could be determined directly from obtained interaction information about the interaction between the MRI pulse sequences and biological tissue. Using such MRI-related information directly could provide an improved respiration signal, as the respiration signal may be related directly to changes in the configuration of the abdominothoracic anatomy that are relevant to MR imaging of the abdominothoracic anatomy. Thus, a degree of view-sharing determined from such a signal may be preferred as it may be governed directly by the sorts of changes in the MR signal that are relevant to decreasing (or increasing) the degree of view sharing, and there may be a reduced or abolished need to calibrate any relationship between the generated respiratory signal and the determined threshold frequency or other characteristic of view sharing relative to sensor-based respiratory signals.

Such a respiratory signal could be determined based on information in k-space near the origin of k-space (e.g., the DC-component of the MR signal in k-space). Such near-origin information may be related to the overall contrast or low-frequency content of the image, which may in turn be related to the overall configuration or phase within the respiratory cycle of the imaged anatomy. So, a value of the respiratory signal could be determined, for a particular period of time, based on the magnitude of DC content (e.g., content at or near the origin in k-space) in obtained interaction information that corresponds to a magnetic resonance imaging pulse sequence provided to the biological tissue during the particular period of time.

Figure 3D:
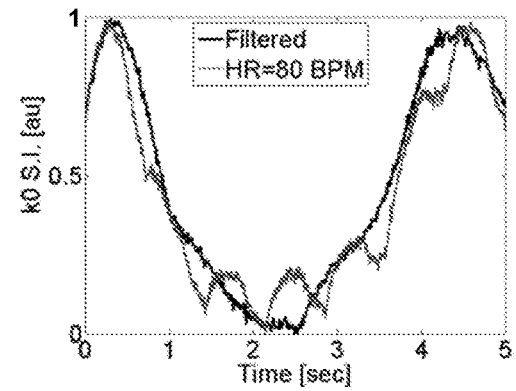
FIG. 3D shows a breathing signal extracted from simulated MRI data.

FIG. 3D illustrates an example of a simulated respiratory signal obtained using such a method. FIG. 3D shows an unfiltered version of such a signal, and a version that has been band-pass filtered to remove heartbeat-related signal content. The filtered or unfiltered respiratory signal could be used to select reference phases for MRI pulse sequences, to determine a degree of view sharing for particular reference phases and/or MRI pulse sequences, to determine a respiration rate or timing of a person, or to facilitate some other applications as described elsewhere herein. For example, the respiratory signal could be used to determine normalized differences, $s_n$ or $\overline{\Delta s_n}$, as illustrated in FIGS. 3B and 3C.

Figure 3E:
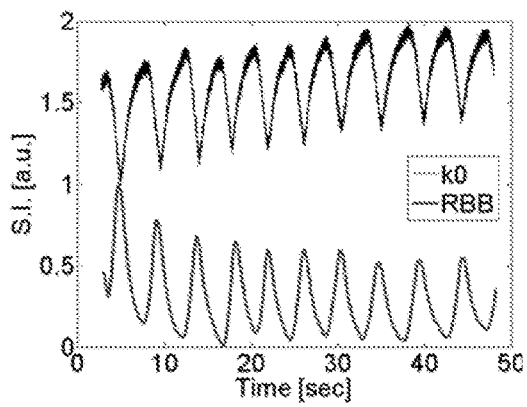
FIG. 3E shows a comparison of two breathing signals generated via different means.
Figure 3F:
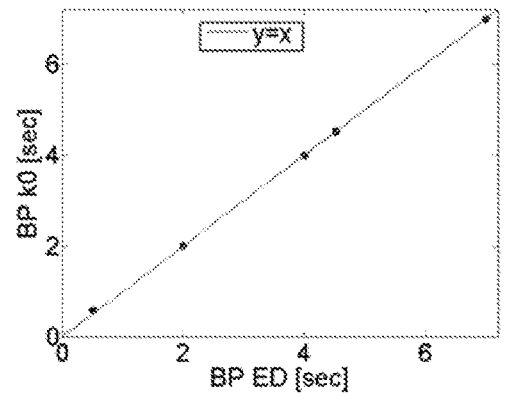
FIG. 3F shows a comparison of breathing rates determined from two breathing signals generated via different means.

FIG. 3E illustrates a respiratory signal determined from MRI data as described above ("k0") and respiratory signal obtained from a respiratory bellows belt ("RBB"). The signals correspond well. FIG. 3F shows the excellent linear correspondence between breathing rates determined based on the respiratory signal determined from the MRI data ("BP k0") and breathing rates determined based on the respiratory external device ("BP ED").

IV. Experimental and Simulation Results

The methods described herein provide improvements in the imaging of abdominothoracic tissues during breathing. These improvements can include improving the resolution and ability to determine the location of tissues (e.g., of tumors) for given imaging parameters (e.g., pulse number, duration) relative to the methods of the prior art.

Figure 4A:
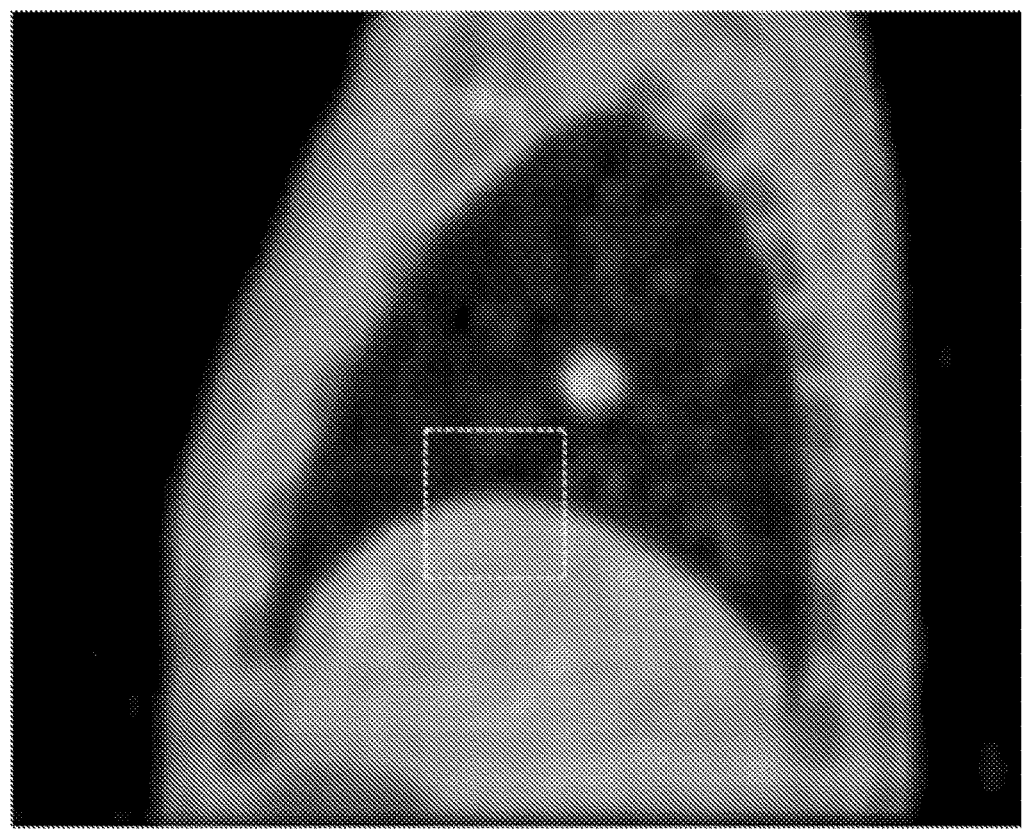
FIG. 4A shows an example MR image of a simulated biological tissue.

FIG. 4A shows an example image of simulated abdominothoracic tissues. The simulation was configured to vary the configuration of the tissues across a simulated respiratory cycle, and included a simulated growth (the bright dot in the middle of the dark field at the middle of FIG. 4A) that moved in time with the respiratory cycle. The performance of the techniques described herein was evaluated using the simulated abdominothoracic tissues.

Figure 4B:
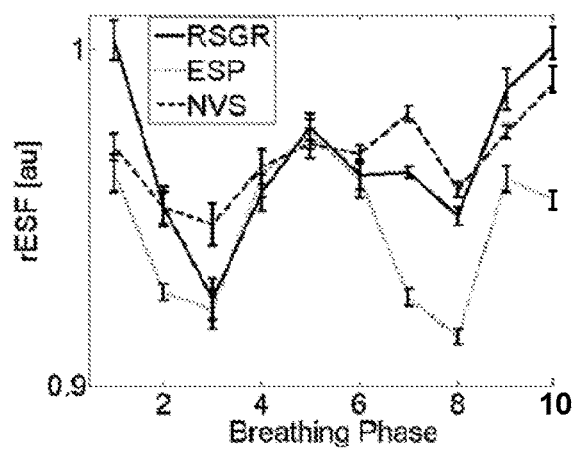
FIG. 4B shows a metric of simulated imaging quality for multiple different imaging techniques as a function of simulated respiratory phase.
Figure 4C:
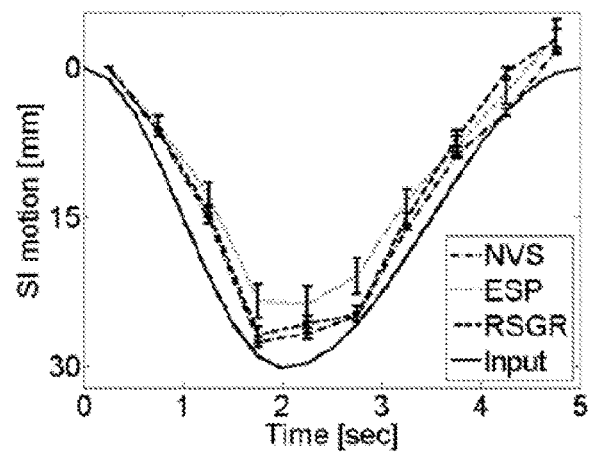
FIG. 4C shows an estimate of simulated tissue displacement over time as determined based on multiple different imaging techniques.

FIG. 4B illustrates the relative performance of the techniques described herein as regards spatial resolution. FIG. 4B shows the reconstruction edge-spread function ("rESF") calculated across the simulated tissue border located within the box shown inset in FIG. 4A. The rESF was calculated as the average of ten different vertical lines within the indicated region; higher values of rESF indicate higher spatial resolution. The rESF was evaluated for each of ten reference phases of simulated respiration when calculating the view-sharing threshold frequency on a per-phase basis ("RSGR", respiratory-signal guided reconstruction), when using a single view-sharing threshold frequency in-common across the reference phases ("ESP", equal sharing from all phases), or when using no view sharing at all ("NVS", no view sharing). FIG. 4C shows the center of mass of the simulated growth over time (true value plotted as "Input") as determined from images generated using the three different methods.

Figures 5A, 5B:
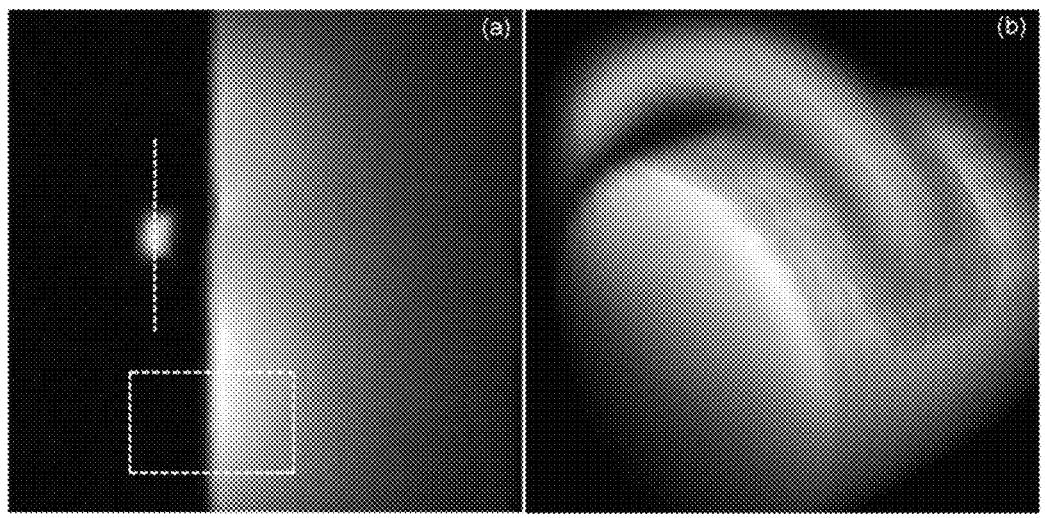
FIG. 5A shows an example MR image of a test element.
FIG. 5B shows an example MR image of the test element shown in FIG. 5A.

FIG. 5A shows an example cross-sectional image of a physical phantom imaged using the methods described herein. The physical phantom included a 2 mm inner diameter polyethylene tube placed over another tube with an inner diameter of 15 mm. Both tubes were filled with a 5 mM $CuSO_4$ solution and oriented such that their long axes were on orthogonal planes. The phantom was connected to a linear actuator which translated the phantom in space according to a sinusoidal motion trajectory with a 2.5 mm amplitude (5.0 mm displacement) and a period of 5 seconds. Motion direction was along the longitudinal axis of the large tube. This configuration simulates a small moving target of known dimensions (2 mm tube) next to a relatively stable and stationary structure (15 mm tube). FIG. 5B shows an MR-based rendering of the surface of the physical phantom. The phantom was imaged using a 7T MR scanner (Bruker BioSpin MRI GmbH, Ettlingen, Germany) equipped with self-shielded gradient coils having a maximum gradient strength of 450 mT/m and rise time of 110 μsec. An actively detuned volume RF coil (linear transmit, ID=72 mm) was used in conjunction with a four-element coil (2×2 linear array, 10×10 mm loops) for surface receive. The acquisition parameters were: FOV=30 mm3, matrix=1283, TR/TE=5.0/0.02 ms, BW=100 kHz, NEX=1, α=10°, and total scan time=2.1 mins.

Figure 5C:
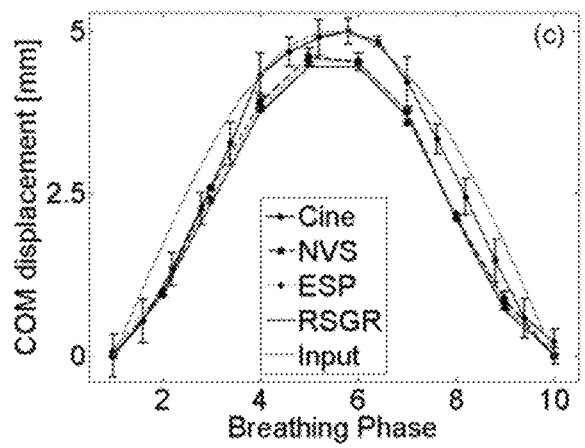
FIG. 5C shows an estimate of test element displacement over time as determined based on multiple different imaging techniques.

FIG. 5C shows the center of mass of the physical phantom over time (true value plotted as "Input") for each of ten respiratory reference phases as determined from images generated using the three different methods. The location of the physical phantom was also determined using cine-MRI ("Cine") according to following parameters: FLASH pulse sequence, FOV=30 mm3, matrix=90×90, single slice imaging, slice thickness=1 mm, TR/TE=3.0/1.8 ms, BW=100 kHz, NEX=1, α=10°, and frame rate ~3 fps.

Figure 5D:
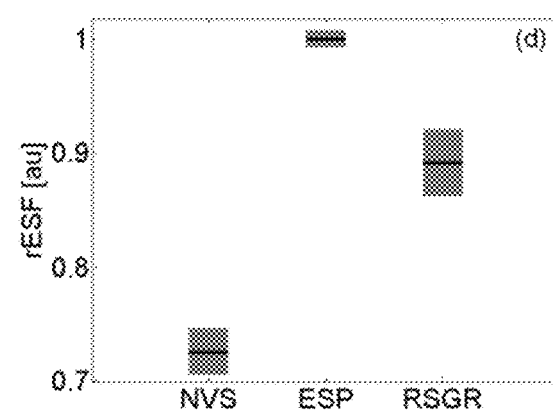
FIG. 5D shows the quality of imaging of a test element using multiple different imaging techniques.

FIG. 5D illustrates the relative performance of the techniques described herein as regards spatial resolution. FIG. 5D shows the mean and standard error of the reconstruction edge-spread function ("rESF") calculated across the simulated tissue border located within the box shown inset in FIG. 5A, across ten different respiratory reference phases, as imaged using the three different methods.

Figure 5E:
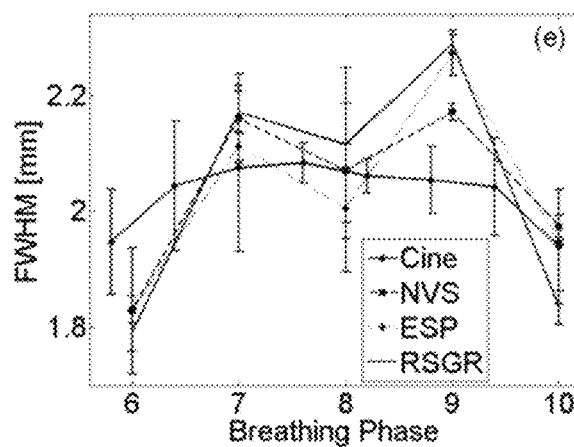
FIG. 5E shows the variation in determined width of a test element using multiple different imaging techniques as a function of simulated respiratory phase.

FIG. 5E illustrates the relative performance of the techniques described herein as regards the determination of the size of a moving object. FIG. 5E shows the degree of elongation (the full width at half maximum, "FWHM") of the physical phantom in the longitudinal direction (along the direction indicated by the dashed vertical line in FIG. 5A). The FWHM was evaluated for each of the ten reference phases of simulated respiration based on images generated using the methods described herein and using cine-MRI ("Cine").

Figure 6A:
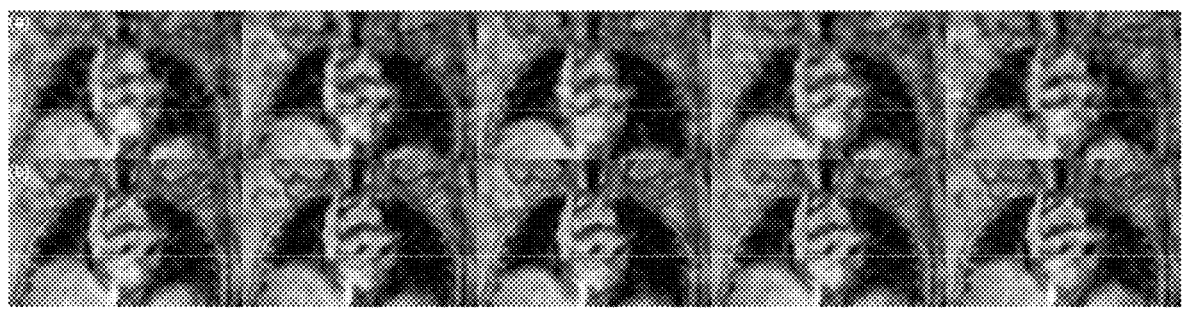
FIG. 6A shows example MR images of biological tissues during breathing.

FIG. 6A shows images, at each of five different respiratory reference phases, of a human torso generated using the methods described herein. A 1.5 T clinical MR scanner equipped with self-shielded gradient coils having a maximum gradient strength of 33 mT/m and maximum slew rate of 120 mT/m was used. An actively detuned receive chest coil was used in conjunction with the body coil for excitation. The acquisition parameters were: FOV=40 cm3, matrix=1283, TR/TE=5.0/0.264 ms, BW=31.25 kHz, NEX=1, α=10°, and total scan time=2.1 mins. The upper row images were generated without view sharing, and the lower row were generated according to the respiratory-signal guided reconstruction ("RSGS") method. It is evident that the RSGS method improves the image quality.

Figure 6B:
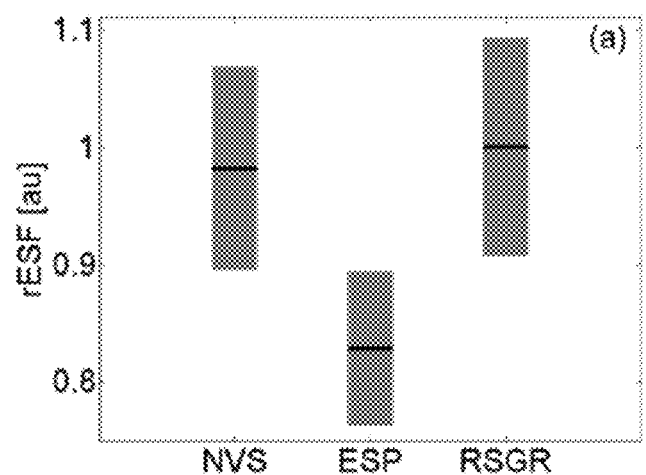
FIG. 6B shows the quality of imaging of the biological tissue shown in FIG. 6A using multiple different imaging techniques.

FIG. 6B illustrates the relative performance of the techniques described herein as regards spatial resolution in the human test images. FIG. 6B shows the mean and standard error of the reconstruction edge-spread function ("rESF") calculated across the liver-lung tissue border shown in FIG. 6A, across ten different respiratory reference phases, as imaged using the three different methods. The RSGS method is able to provide improved images (as illustrated in FIG. 6A) without degrading the rESF.

Figure 6C:
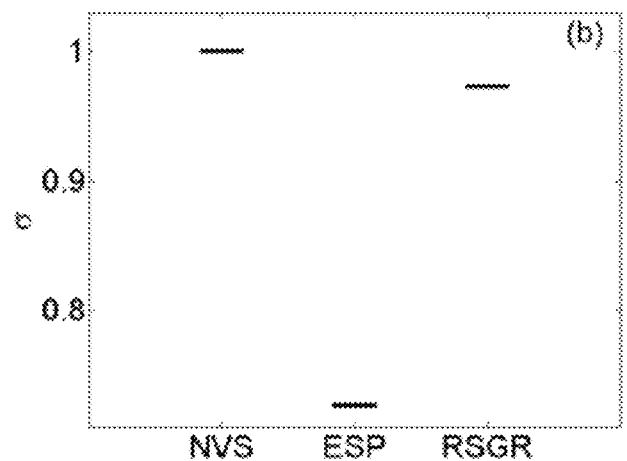
FIG. 6C shows a noise floor of images of the biological tissue shown in FIG. 6A using multiple different imaging techniques.

FIG. 6C illustrates the relative performance of the techniques described herein as regards noise level in the human test images floor. FIG. 6C shows the standard deviation of signal intensity (across phases) in a large background region with no NMR signal. The RSGS method is able to provide improved images (as illustrated in FIG. 6A) without increasing the noise floor.

Subashi, E., Liu, Y, Segars, P., Yin, F., Cai, J., "Optimal k-Space Filtering for View-Sharing Techniques in Projection Encoding 4D MRI," MR in RT Symposium, Ann-Arbor, Mich., June 2016, and "High Spatiotemporal Resolution Self-Sorted 4D MRI," is also incorporated herein by reference (Subashi, E., Liu, L., Robertson, S., Segars, P., Driehuys, B., Yin, F., Cai, J., "High Spatiotemporal Resolution Self-Sorted 4D MRI," American Association of Physicists in Medicine Annual Meeting, Washington D.C., July 2016 are both incorporated herein by reference.

All references cited herein are incorporated by reference. In addition, the invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims.

V. Conclusion

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A method comprising:
  obtaining interaction information indicative of a plurality of interactions between a biological tissue and respective different magnetic resonance imaging pulse sequences, wherein the obtained interaction information comprises imaging information about the biological tissue at discrete points along a plurality of different radial trajectories in k-space, wherein each magnetic resonance imaging pulse sequence corresponds to a respective one of the radial trajectories in k-space;

obtaining a respiratory signal related to respiratory activity of the biological tissue;

based on the respiratory signal, selecting a respective reference phase for each of the magnetic resonance imaging pulse sequences, wherein the respective reference phases are selected from a plurality of respiratory phases; and generating a first image of the biological tissue for a first reference phase in the plurality of respiratory phases, wherein generating the first image comprises:

generating imaging information about the biological tissue during the first reference phase at a set of points in k-space based on a first portion of the obtained interaction information and a second portion of the obtained interaction information, wherein the first portion comprises information about at least two magnetic resonance imaging pulse sequences corresponding to the first reference phase, and wherein the second portion comprises information about at least one of the magnetic resonance imaging pulse sequences corresponding to a second reference phase that differs from the first reference phase; and transforming the generated imaging information to generate the first image.

2. The method of claim 1, wherein transforming the generated imaging information to generate the first image comprises:

based on the generated imaging information at the set of points in k-space, determining further imaging information about the biological tissue during the first reference phase at a second set of points in k-space, wherein the second set of points in k-space are arranged within k-space as a regular, orthogonal grid; and using a Fourier transform to transform the determined further imaging information to generate the first image.

3. The method of claim 1, wherein the second portion of the obtained interaction information comprises interaction information corresponding to points in k-space that are separated from the origin of k-space by more than a first threshold frequency.

4. The method of claim 3, wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to a third reference phase that differs from the first and second reference phases, wherein the third portion of the obtained interaction information comprises interaction information corresponding to points in k-space that are separated from the origin of k-space by more than the first threshold frequency.

5. The method of claim 3, further comprising:

determining, based on the respiratory signal, the first threshold frequency for the second reference phase, wherein the first threshold frequency is determined based on a difference between an average value of portions of the respiratory signal corresponding to the first reference phase and an average value of portions of the respiratory signal corresponding to the second reference phase;

determining, based on the respiratory signal, a second threshold frequency for a third reference phase,
wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase; and wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to the third reference phase, wherein the third portion of the obtained interaction information comprises interaction information corresponding to points in k-space that are separated from the origin of k-space by more than the second threshold frequency.

6. The method of claim 1, further comprising:

for a given magnetic resonance imaging pulse sequence, determining a magnitude of DC content in the obtained interaction information corresponding to the given magnetic resonance imaging pulse sequence, wherein selecting a reference phase for the given magnetic resonance imaging pulse sequence comprises selecting the reference phase for the given magnetic resonance imaging pulse sequence based on the determined magnitude of DC content.

7. The method of claim 6, wherein obtaining the respiratory signal related to respiratory activity of the biological tissue comprises determining the respiratory signal based on the determined magnitude of DC content, and wherein the method further comprises:

determining, based on the respiratory signal, a first threshold frequency for the second reference phase, wherein the first threshold frequency is determined based on a difference between an average value of portions of the respiratory signal corresponding to the first reference phase and an average value of portions of the respiratory signal corresponding to the second reference phase; and determining, based on the respiratory signal, a second threshold frequency for a third reference phase, wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase;

wherein the second portion of the obtained interaction information comprises interaction information corresponding to points in k-space that are separated from the origin of k-space by more than the first threshold frequency; and wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to the third reference phase, wherein the third portion of the obtained interaction information comprises interaction information corresponding to points in k-space that are separated from the origin of k-space by more than the second threshold frequency.

8. The method of claim 6, wherein the given magnetic resonance imaging pulse sequence corresponds to a third reference phase that differs from the first reference phase, wherein obtaining the respiratory signal related to respiratory activity of the biological tissue comprises determining the respiratory signal based on the determined magnitude of DC content in the obtained interaction information, and wherein the method further comprises:
  determining a threshold frequency for the given magnetic resonance imaging pulse sequence based on the determined magnitude of DC content in the obtained interaction information, wherein the threshold frequency is determined based on a difference between an average value of portions of the respiratory signal corresponding to the first reference phase and a value of a portion of the respiratory signal corresponding to the given magnetic resonance imaging pulse sequence;
  wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about the given magnetic resonance imaging pulse sequence, wherein the third portion of the obtained interaction information comprises interaction information corresponding to points in k-space that are separated from the origin of k-space by more than the threshold frequency.

9. A non-transitory computer-readable medium having instructions stored thereon that, upon execution by at least one processor, causes performance of operations, the operations comprising:
  obtaining interaction information indicative of a plurality of interactions between a biological tissue and respective different magnetic resonance imaging pulse sequences, wherein the obtained interaction information comprises imaging information about the biological tissue at discrete points along a plurality of different radial trajectories in k-space, wherein each magnetic resonance imaging pulse sequence corresponds to a respective one of the radial trajectories in k-space;
  obtaining a respiratory signal related to respiratory activity of the biological tissue;
  based on the respiratory signal, selecting a respective reference phase for each of the magnetic resonance imaging pulse sequences, wherein the respective reference phases are selected from a plurality of respiratory phases; and
  generating a first image of the biological tissue for a first reference phase in the plurality of respiratory phases, wherein generating the first image comprises:
    generating imaging information about the biological tissue during the first reference phase at a set of points in k-space based on a first portion of the obtained interaction information and a second portion of the obtained interaction information, wherein the first portion comprises information about at least two magnetic resonance imaging pulse sequences corresponding to the first reference phase, and wherein the second portion comprises information about at least one of the magnetic resonance imaging pulse sequences corresponding to a second reference phase that differs from the first reference phase; and
    transforming the generated imaging information to generate the first image.

10. The non-transitory computer-readable medium of claim 9, wherein the second portion of the obtained interaction information comprises interaction information corresponding to points in k-space that are separated from the origin of k-space by more than a first threshold frequency.

11. The non-transitory computer-readable medium of claim 10, wherein the operations further comprise:
  determining, based on the respiratory signal, the first threshold frequency for the second reference phase, wherein the first threshold frequency is determined based on a difference between an average value of portions of the respiratory signal corresponding to the first reference phase and an average value of portions of the respiratory signal corresponding to the second reference phase;
  determining, based on the respiratory signal, a second threshold frequency for a third reference phase, wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase; and
  wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to the third reference phase, wherein the third portion of the obtained interaction information comprises interaction information corresponding to points in k-space that are separated from the origin of k-space by more than the second threshold frequency.

12. The non-transitory computer-readable medium of claim 9, wherein the operations further comprise:
  for a given magnetic resonance imaging pulse sequence, determining a magnitude of DC content in the obtained interaction information, wherein the magnitude of DC content corresponds to the given magnetic resonance imaging pulse sequence, wherein selecting a reference phase for the given magnetic resonance imaging pulse sequence comprises selecting the reference phase for the given magnetic resonance imaging pulse sequence based on the determined magnitude of DC content in the obtained interaction information corresponding to the given magnetic resonance imaging pulse sequence.

13. The non-transitory computer-readable medium of claim 12, wherein obtaining the respiratory signal related to respiratory activity of the biological tissue comprises determining the respiratory signal based on the determined magnitude of DC content in the obtained interaction information, and wherein the operations further comprise:
  determining, based on the respiratory signal, a first threshold frequency for the second reference phase, wherein the first threshold frequency is determined based on a difference between an average value of portions of the respiratory signal corresponding to the first reference phase and an average value of portions of the respiratory signal corresponding to the second reference phase; and determining, based on the respiratory signal, a second threshold frequency for a third reference phase, wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase;

wherein the second portion of the obtained interaction information comprises interaction information corresponding to points in k-space that are separated from the origin of k-space by more than the first threshold frequency; and wherein generating imaging information about the biological tissue during the first reference phase at the set of points in k-space comprises generating the imaging information about the biological tissue during the first reference phase at a set of points in k-space based on a third portion of the obtained interaction information, wherein the third portion comprises information about at least one of the magnetic resonance imaging pulse sequences corresponding to the third reference phase, wherein the third portion of the obtained interaction information comprises interaction information corresponding to points in k-space that are separated from the origin of k-space by more than the second threshold frequency.

14. A method comprising:

causing a pulse generator to emit a plurality of different magnetic resonance imaging pulse sequences such that the plurality of magnetic resonance imaging pulse sequences interact with a biological tissue, wherein each magnetic resonance imaging pulse sequence corresponds to a respective radial trajectory in k-space;

obtaining interaction information indicative of a plurality of interactions between the biological tissue and the magnetic resonance imaging pulse sequences, wherein the obtained interaction information comprises imaging information about the biological tissue at discrete points along a plurality of different radial trajectories in k-space, wherein each of the different radial trajectories in k-space corresponds to at least one of the magnetic resonance imaging pulse sequences;

obtaining a respiratory signal related to respiratory activity of the biological tissue;

based on the respiratory signal, selecting a respective reference phase for each of the magnetic resonance imaging pulse sequences, wherein the respective reference phases are selected from a plurality of respiratory phases; and generating a first image of the biological tissue for a first reference phase in the plurality of respiratory phases, wherein generating the first image comprises:

generating imaging information about the biological tissue during the first reference phase at a set of points in k-space based on a first portion of the obtained interaction information and a second portion of the obtained interaction information, wherein the first portion comprises information about at least two magnetic resonance imaging pulse sequences corresponding to the first reference phase, and wherein the second portion comprises information about at least one of the magnetic resonance imaging pulse sequences corresponding to a second reference phase that differs from the first reference phase; and transforming the generated imaging information to generate the first image.

15. The method of claim 14, wherein the respective radial trajectory in k-space of each of the magnetic resonance imaging pulse sequences is characterized by a respective angle in k-space, and wherein a set of the angles characterizing the respective radial trajectories of the magnetic resonance imaging pulse sequences corresponds to a quasi-random sampling of angles in k-space.

16. The method of claim 14, wherein the respective radial trajectory in k-space of at least one of the magnetic resonance imaging pulse sequences comprises a spiral trajectory.

17. The method of claim 14, wherein the second portion of the obtained interaction information comprises interaction information corresponding to points in k-space that are separated from the origin of k-space by more than a first threshold frequency.

18. The method of claim 17, further comprising:

determining, based on the respiratory signal, the first threshold frequency for the second reference phase, wherein the first threshold frequency is determined based on a difference between an average value of portions of the respiratory signal corresponding to the first reference phase and an average value of portions of the respiratory signal corresponding to the second reference phase;

determining, based on the respiratory signal, a second threshold frequency for a third reference phase, wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase; and wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to a third reference phase, wherein the third portion of the obtained interaction information comprises interaction information corresponding to the points in k-space that are separated from the origin of k-space by more than the first threshold frequency.

19. The method of claim 14, further comprising:

for a given magnetic resonance imaging pulse sequence, determining a magnitude of DC content in the obtained interaction information that corresponds to the given magnetic resonance imaging pulse sequence, wherein selecting a reference phase for the given magnetic resonance imaging pulse sequence comprises selecting the reference phase for the given magnetic resonance imaging pulse sequence based on the determined magnitude of DC content in the obtained interaction information corresponding to the given magnetic resonance imaging pulse sequence.

20. The method of claim 19, wherein obtaining the respiratory signal related to respiratory activity of the biological tissue comprises determining the respiratory signal based on the determined magnitude of DC content in the obtained interaction information, and wherein the method further comprises:

determining, based on the respiratory signal, a first threshold frequency for the second reference phase, wherein the first threshold frequency is determined based on a difference between an average value of portions of the respiratory signal corresponding to the first reference phase and an average value of portions of the respiratory signal corresponding to the second reference phase; and determining, based on the respiratory signal, a second threshold frequency for a third reference phase, wherein the third reference phase differs from the first and second reference phases, wherein the second threshold frequency is determined based on a difference between the average value of the portions of the respiratory signal corresponding to the first reference phase and an average value of portions of the respiratory signal corresponding to the third reference phase;

wherein the second portion of the obtained interaction information comprises interaction information corresponding to points in k-space that are separated from the origin of k-space by more than the first threshold frequency; and wherein generating imaging information about the biological tissue during the first reference phase at a set of points in k-space comprises generating the imaging information about the biological tissue during the first reference phase at the set of points in k-space based on a third portion of the obtained interaction information, wherein the third portion comprises information about at least one of the magnetic resonance imaging pulse sequences corresponding to the third reference phase, wherein the third portion of the obtained interaction information comprises interaction information corresponding to points in k-space that are separated from the origin of k-space by more than the second threshold frequency.

* * * * *